United States Patent [19]

Kawaguchi et al.

[11] Patent Number: 5,185,344
[45] Date of Patent: Feb. 9, 1993

[54] PHARMACEUTICALLY USEFUL BICYCLOLACTAM DERIVATIVE

[75] Inventors: Akihiro Kawaguchi; Atsushi Satoh, both of Hannou; Makoto Kajitani, Saitama; Mitsugi Yasumoto, Honjo; Junji Yamamoto, Tokushima, all of Japan

[73] Assignee: Taiho Pharmaceutical Company, Ltd., Tokyo, Japan

[21] Appl. No.: 768,074

[22] PCT Filed: Jan. 30, 1991

[86] PCT No.: PCT/JP91/00116
§ 371 Date: Oct. 1, 1991
§ 102(e) Date: Oct. 1, 1991

[87] PCT Pub. No.: WO91/11434
PCT Pub. Date: Aug. 8, 1991

[30] Foreign Application Priority Data

Feb. 2, 1990 [JP] Japan .................................. 2-24754

[51] Int. Cl.$^5$ ..................... A61K 31/435; C07D 22/04
[52] U.S. Cl. .................................. 514/299; 514/421; 546/183; 548/512
[58] Field of Search .................. 546/183; 548/512; 514/299, 421

[56] References Cited

PUBLICATIONS

Kennewell et al., J. Chem. Soc. Perkin Trans. I, pp. 2563-2570 (1982).

Primary Examiner—Bernard Dentz
Attorney, Agent, or Firm—Nikaido, Marmelstein, Murray & Oram

[57] ABSTRACT

The present invention provides a bicyclolactam derivative which has the following formula and is useful as medicaments for treating senile dementia, i.e., as cerebral function improving agents and cerebral metabolism activators or anoxic brain damage protectives

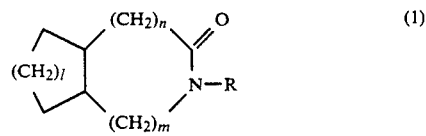

wherein R is benzoyl group which may be substituted with halogen atom, lower alkyl group, lower alkoxyl group, nitro group, cyano group or amino group; l is 1 or 2; m is 0 or 1; and n is 0, 1 or 2, provided that m and n are not 0 at the same time.

5 Claims, No Drawings

PHARMACEUTICALLY USEFUL BICYCLOLACTAM DERIVATIVE

TECHNICAL FIELD

The present invention relates to a novel bicyclolactam derivative. The present compound has cerebral function improving effect, cerebral metabolism activating or anoxic brain damage protecting effect and effect against senile dementia.

BACKGROUND ART

With an increase in the population of advanced ages in recent years, patients with senile dementia increase in number, posing a serious problem medically and socially. Although various antidementia drugs have been investigated and developed in view of the situation, no compounds have been provided with satisfactory efficacy. It has been strongly desired to develop medicaments for treating the disease.

An object of the present invention is to provide novel bicyclolactam derivatives which are very useful as medicaments for treating senile dementia, i.e., as cerebral function improving agents and cerebral metabolism activators or anoxic brain damage protectives.

DISCLOSURE OF THE INVENTION

The present invention provides a bicyclolactam derivative represented by the formula

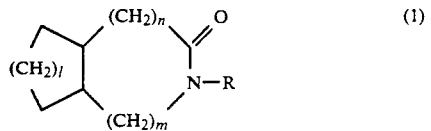

wherein R is benzoyl group which may be substituted with halogen atom, lower alkyl group, lower alkoxyl group, nitro group, cyano group or amino group; $l$ is 1 or 2; m is 0 or 1; and n is 0, 1 or 2, provided that m and n are not 0 at the same time.

The above bicyclolactam derivative of the formula (1) includes stereoisomers due to the presence of bicyclo ring and optical isomers derived from asymmetric carbon atom and all of the isomers are included in the present invention.

In the invention, examples of halogen atoms which are a substituent of benzoyl group represented by R are fluorine, chlorine, bromine and iodine atom. Examples of lower alkyl groups are preferably a straight-chain or branched-chain alkyl group having 1 to 6 carbon atoms such as methyl, ethyl, n-propyl, isopropyl, n-butyl, isobutyl, sec-butyl, tert-butyl, pentyl, isopentyl and hexyl group. Examples of lower alkoxyl groups are preferably a straight-chain or branched-chain alkoxyl group having 1 to 6 carbon atoms such as methoxy, ethoxy, n-propoxy, isopropoxy, n-butoxy, isobutoxy, sec-butoxy, tert-butoxy, pentyloxy, isopentyloxy and hexyloxy group. The benzoyl group preferably has 1 to 3 substituents.

Among the compounds of the formula (1), preferable are those wherein R is benzoyl group which is substituted with lower alkoxyl group or amino group, $l$ is 1 or 2, m is 0 or 1, and n is 0 or 2. Further, more preferable are those wherein R is benzoyl group which is substituted with lower alkoxyl group, when $l$ is 1, m is 0, and n is 2, or when $l$ is 2, m is 1, and n is 0.

Further, we have found that the present compound of the formula (1) has an excellent cerebral function improving effect, cerebral metabolism activating or anoxic brain damage protecting effect and effect against senile dementia.

Accordingly, the present invention provides a cerebral function improving composition and a cerebral metabolism activating or anoxic brain damage protecting composition each comprising an effective amount of a compound of the formula (1) and a pharmacologically acceptable carrier.

The present invention further provides a method of improving cerebral functions and activating cerebral metabolism or protecting anoxic brain damage characterized by administering an effective amount of a compound of the formula (1).

The compounds of the formula (1) have pharmacological activities to ameliorate:
(1) cerebral damage in anoxia, and
(2) amnesia induced by a scopolamine in passive condition avoidance response.

These pharmacological properties are useful for activating injured nervous cells and ameliorate memory and learning disturbances.

Accordingly, the compounds of the present invention are usable not only as medicaments for use in treating deterioration of intelligence or neurasthenia, amnesia, senile dementia or intellectual fatigue, cerebrovascular dementia, aftereffects of encephalopathy and Alzheimer's disease but also as medicaments for improving other cerebral functions or for activating cerebral metabolism or protecting anoxic brain damage.

The bicyclolactam derivative (1) of the present invention can be prepared, for example, by the following reaction process.

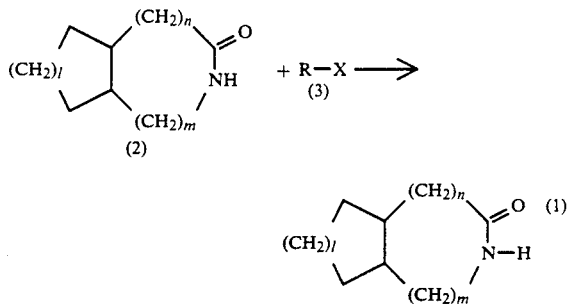

wherein R, $l$, m and n are as defined above, X is halogen atom.

Bicyclolactam compound (2) is a known compound and is easily prepared by methods disclosed in Journal of American Chemical Society, 77, 409 (1955), Yakugaku Zasshi, 84, 674 (1964) and Journal of Chemical Society Perkin Transactions I 11, 2563 (1982). The present compound of the formula (1) can be prepared by reacting the bicyclolactam compound (2) with the halide compound (3), in the presence of a base in an appropriate solvent.

The solvent is not limited specifically insofar as it does not participate in the reaction. Examples of solvents generally useful are hydrocarbon halides such as dichloromethane and chloroform, ethers such as ethyl ether and tetrahydrofuran, aromatic hydrocarbons such as benzene and toluene, aprotic polar solvents such as N,N-dimethylformamide and dimethylsulfoxide.

As to the proportion of the compound (2) and the halide compound (3), it is usual to use 0.5 to 2 moles, preferably one mole of the compound (3) per mole of the compound (2). Examples of bases are organic amines such as triethylamine, pyridine and 4-dimethylaminopyridine, and inorganic bases such as sodium hydride and sodium amide. The amount of the base is usually 0.5 to 2 moles, preferably one mole per mole of the compound (2). The reaction temperature is 0° to 150° C., preferably 50° to 100° C. The reaction time is 1 to 48 hours, preferably 2 to 12 hours.

The present compound can be readily purified or isolated by a usual separating method, such as extraction, distillation, recrystallization, gas or liquid column chromatography or the like.

When the present compound is to be administered for the purpose of treating deterioration of intelligence or neurasthenia, amnesia, senile dementia or intellectual fatigue, and Alzheimer's disease, the compound is administered in the form of a pharmacological preparation such as oral preparation, injection, suppository or the like. These preparations can be produced by conventional methods already known to those skilled in the art.

Solid preparations for oral administration can be produced in a usual manner by adding to the present compound an excipient, and when required, a binder, disintegrator, lubricant, coloring agent, corrigent, flavor and the like, and making the mixture into tablets, granules, powders or an encapsulated preparation. Such additives are those generally used in the art. Examples of useful excipients are lactose, sucrose, sodium chloride, glucose, starch, calcium carbonate, kaolin, microcrystalline cellulose, silicic acid and the like. Examples of useful binders are water, ethanol, propanol, syrup, glucose solution, starch solution, gelatin solution, carboxymethyl cellulose, hydroxypropyl cellulose, hydroxypropyl starch, methyl cellulose, ethyl cellulose, shellac, calcium phosphate, polyvinylpyrrolidone and the like. Examples of useful disintergrators are dried starch, sodium alginate, agar powder, sodium hydrogencarbonate, calcium carbonate, sodium laurylsulfate, stearic acid monoglyceride, starch, lactose and the like. Examples of useful lubricants are purified talc, stearic acid salts, borax, polyethylene glycol and the like. Examples of useful corrigents are sucrose, bitter orange peel, citric acid, tartaric acid and the like.

Liquid preparations for oral administration can be produced by adding a corrigent, buffer, stabilizer, flavor and the like to the present compound, and making the mixture into a liquid oral preparation, syrup, elixir or the like. Examples of useful corrigents are those exemplified above. Exemplary of useful buffers are sodium citrate and the like. Examples of useful stabilizers are tragacanth, gum arabic, gelatin and the like.

Injections can be produced in a usual manner by adding a pH adjusting agent, buffer, stabilizer, isotonic agent, local anesthetic and the like to the present compound, and formulating the mixture into a preparation for subcutaneous, intramuscular or intravenous injection. Examples of useful pH adjusting agents and buffers are sodium citrate, sodium acetate, sodium phosphate and the like. Examples of useful stabilizers ares sodium pyrosulfite, EDTA, thioglycolic acid, thiolactic acid and the like. Examples of useful local anesthetics are procaine hydrochloride, lidocaine hydrochloride and the like.

Suppositories can be prepared by adding to the present compound a pharmaceutical carrier known in the art, such as polyethylene ghycol, lanolin, cacao fat, fatty acid triglyceride or the like, along with Tween (registered trademark) or like surfactant and the like when desired, and treating the mixture in the usual manner.

Although the amount of the present compound to be contained in the unit form of each preparation varies with the symptoms of the patient, the type of preparation, etc., the amount is generally preferably about 1 to about 300 mg for oral administration, about 1 to about 50 mg for injection or about 1 to 200 mg for suppositories, per unit of the preparation. The dosage of the compound to be given in the form of such a preparation can not be determined specifically but varies with the symptoms, weight, age, sex, etc. of the patient. However, it is given usually at a dose of about 0.5 to about 1000 mg, preferably 1 to 500 mg, per day for adults, preferably once or in up to four divided doses. Best mode for carrying out the invention The present invention will be described below in greater detail with reference to examples wherein bicyclolactam derivatives of the formula (1) were prepared, and to the tests conducted to determine the antiamnesia activity of compounds 3 and 12 and the acute toxicity test thereof. Table 1 shows the compounds prepared in the examples. In the elementary analysis in the Table, upper column shows analyzed value, lower column calculated value.

EXAMPLE 1

In 100 ml of dichloromethane were dissolved 3.0 g (19.6 mmol) of 2-azabicyclo-[4.4.0]-decane-3-one [Journal of American Chemical Society, 77, 409 (1955)], 3.35 g (19.6 mmol) of p-methoxybenzoyl chloride and 2.38 g (23.5 mmol) of triethylamine and the solution was heated under reflux for 2 hours. After cooled, and organic layer was washed with water, 10% hydrochloric acid and saturated aqueous solution of sodium chloride, and dried over anhydrous magnesium sulfate. After removing the solvent, the resulting residue was chromatographed over silica gel to obtain 4.5 g (yield 80% ) of 2-(4-methoxybenzol)-2-azabicyclo-[4.4.0]-decane-3-3-one (Compound 1) from hexane-ethyl acetate (3:1) eluate. Table 1 shows melting point and elementary analysis of the compound.

EXAMPLE 2

Compound 2 was obtained in the same manner as in Example 1 with use of, as a starting material, 2-azabicyclo-[3.3.0]-octane-3-one [Yakugaku Zasshi, 84, 674 (1964]. Table 1 shows melting point and elementary analysis of the compound.

EXAMPLE 3

A known compound, 2-azabicyclo-[4.3.0]-nonane-3-one was prepared by the method disclosed in Journal of American Chemical Society, 77, 409 (1955).

Namely, to a solution of 50 ml (0.35 mol) of ethyl cyclopentanone-2-carboxylate in 130 ml of dioxane was added 3.8 ml of Triton B. Then, to the solution was added 27.1 ml (0.242 mol) of acrylonitrile in 50 ml of dioxane. The solution was stirred at room temperature for 12 hours, and extracted with ether after 100 ml of 10% hydrochloride acid was added thereto. An organic layer was dried over anhydrous magnesium sulfate. After removing the solvent, 300 ml of conc. hydrochloric acid was added to the residue and the mixture was heated under reflux for 24 hours. After cooling, the mixture was extracted with ether and 5% aqueous solution of sodium hydroxide was added to the ether layer and the mixture was stirred. An aqueous layer was made acidic with addition of 10% hydrochloric acid, and then the mixture was extracted with ethyl acetate. An organic layer was dried over anhydrous magnesium sulfate. After removing the solvent, the residue was dissolved in 150 ml of ethanol and 10 ml of conc. sulfuric acid was added thereto. The mixture was heated under reflux for 14 hours, and then ethanol was removed therefrom after cooling, and ethyl acetate was added thereto. The mixture was washed with 10% aqueous solution of sodium hydroxide and dried over anhydrous magnesium sulfate. After removing the solvent, the resulting residue was chromatographed over silica gel to obtain 45 g (yield 70% of ethyl 2-oxocyclopentanepropionate from hexane-ethyl acetate (4:1) eluate. In 150 ml 80% ethanol was dissolved 5.5 g (30 mmol) of this compound. To the solution were added 4.17 g (60 mmol) of hydroxylamine hydrochloride and 2.7 g (33 mmol) of sodim acetate and the mixture was stirred at room temperature over night. After removing ethanol, the mixture was extracted with ethyl acetate and dried over anhydrous magnesium sulfate. After removing the solvent, the resulting residue was chromatographed over silica gel to obtain 5 g (yield 84%) of ethyl 2-hydroxyiminocyclopentanepropionate from hexane-ethyl acetate (6:1) eluate. In 15 ml of anhydrous ethanol was dissolved 4.4 g of this compound and the solution was stirred at 50° C. for 4 hours under a hydrogen pressure of 120 atm. with use of Raney nickel (W2) as a catalyst. After removing Raney nickel by filtration and removing the solvent, the resulting residue was chromatographed over silica gel to obtain 0.95 g (yield 31%) of 2-azabicyclo-[4.3.0]-nonane-3-one from ethyl acetate eluate.

Compounds 3 to 10 were obtained in the same manner as in Example 1 with use of the above compound as a starting material. Table 1 shows elementary analysis and Table 2 gives NMR spectrum data of Compound 3.

EXAMPLE 4

A known compound, 2-azabicyclo-[3.4.0]-nonane-3-one was prepared by the method disclosed in Yakugaku Zasshi, 84, 674 (1964).

Namely, the desired 2-azabicyclo-[3.4.0]-nonane-3-one was prepared in the same manner as in Example 3, with use of, as a starting material, ethyl 2-oxocyclohexylacetate.

Compound 11 was obtained in the same manner as in Example 1 with use of the above compound as a starting material. Table 1 shows elementary analysis and Table 2 gives NMR spectrum data of Compound 11.

EXAMPLE 5

Compound 12was obtained in the same manner as in Example 1 with use of, as a starting material, 3-azabicyclo-[3.4.0]-nonane-2-one [Journal of Chemical Society Perkin Transactions I 11, 2563 (1982)]. Table 1 shows melting point and elementary analysis of the compound.

EXAMPLE 6

The compound obtained in Example 3 was further ODS chromatographed to obtain the following Compound 3a (yield 15%) and Compound 3d (yield 50%) from methanol-water (1:1) eluate. Table 1 shows melting point and elementary analysis of the compounds.

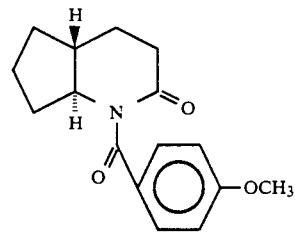

(3a)

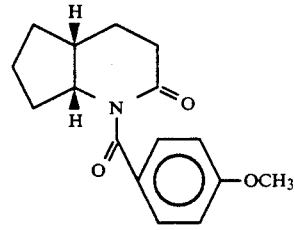

(3b)

In Table 1, Me and OMe stand for methyl and methoxy respectively. In the elementary analysis, value in the parenthesis is calculated value.

| Example 7 | |
|---|---|
| Compound 3 | 200 mg |
| Lactose | 500 mg |
| Corn starch | 280 mg |
| Hydroxypropyl cellulose | 20 mg |

The above ingredients in the proportions given were made into a granular preparation by the usual method in an amount of 1000 mg per wrapper.

| Example 8 | |
|---|---|
| Compound 1 | 100 mg |
| Lactose | 85 mg |
| Microcrystalline cellulose | 50 mg |
| Hydroxypropyl starch | 30 mg |
| Talc | 4 mg |
| Magnesium stearate | 1 mg |

By the usual method, the above ingredients in the proportions given were made into tables each weighing 270 mg.

| Example 9 | |
|---|---|
| Compound 12 | 100 mg |
| Lactose | 50 mg |
| Potato starch | 50 mg |
| Microcrystalline cellulose | 109 mg |
| Magnesium stearate | 1 mg |

By the usual method, the above ingredients in the proportions given were made into an encapsulated preparation in an amount of 310 mg in each capsule.

| Example 10 | |
|---|---|
| Compound 9 | 250 mg |
| Fatty acid triglyceride | 750 mg |

By the usual method, the above ingredients in the proportions given were made into suppositories each weighing 1000 mg.

| Example 11 | |
|---|---|
| Compound 11 | 5 mg |
| Sodium chloride | 18 mg |
| Distilled water for injections, | suitable amount |

The above ingredients in the proportions given were made into an injection by the usual method.

TEST EXAMPLE 1

Reversal Activity of Amnesia

1. Animals

Group of 6 to 16 rats (Wistar, males, weighing 170 to 240 g) were used for the experiment. 2. Drug and method of administration Scopolamine was used as dissolved in physiological saline, and the test compound as dissolved or suspended in 0.5% solution of sodium carboxymethyl cellulose.

Scopolamine was subcutaneously given at a dose of 0.5 mg/kg 30 minutes before aquisition trials. The test compound was orally given immediately after the aquisition trials. 3. Method A step-through passive avoidance apparatus was used with reference to Psychopharmacology, 78, 104~111 (1982) and Japan Journal of Pharmacology, 37, 300~302 (1985). The apparatus consisted of a dark compartment (25×12×30 cm) having a grid serving as a floor, and a light compartment (25×12×12 cm) illuminated with 20−W daylight fluorescent lamp from above and separated from the dark compartment by a guillotine door. The rat was subjected to habituation trials about 1 hour before aquisition trails. The habituation was accomplished by placing the rat into the light compartment, opening the door 5 seconds thereafter, closing the door when the four legs completely entered the dark compartment, leaving the rat in the dark compartment for 10 seconds and thereafter taking out the rat. The acquisition trial was accomplished in the same manner as the habituation 1 hour thereafter except that simultaneously when the door was closed upon the movement of the rat into the dark compartment, an unescapable foot shock of 4.5 mA was given to the rat by the floor grit for 1 second.

A retention test was conducted 24 hours after the aquisition trials to measure the step-through latency during which the rat placed into the light compartment remained therein before moving into the dark compartment, i.e., the duration of a passive avoidance reaction. For a rat exhibiting the avoidance reaction for more than a maximum period of time measured (300 seconds), 300 seconds was recorded.

The results were given by amnesia reversal (%) represented by the formula below which was detected in J. Med. Chem. vol. 27 687~691 (1984).

amnesia reversal (%) =

$$\frac{\text{drug group} - \text{base-line control group}}{\text{ceiling control group} - \text{base-line control group}} \times 100$$

drug group: step-through latency (second) of the group administered with scopolamine and the test compound base-line control group: step-through latency (second) of the group administered with scopolamine ceiling control group: step-through latency (second) of the control group (max.; 300 seconds)

Table 3 shows the results in which Compounds 3 and 12 were used. As a control was used Aniracetam which was investigated and considered effective in the present clinical fields.

TABLE 1

| No. | l | m | n | R | m.p. (°C.) | yield (%) | formula | elementary analysis (%) C | H | N |
|---|---|---|---|---|---|---|---|---|---|---|
| 1 | 2 | 0 | 2 | −C(=O)−C$_6$H$_4$−OMe | 90~91 | 80 | C$_{17}$H$_{21}$NO$_3$ | 71.24 (71.06) | 7.50 (7.37) | 4.68 (4.87) |
| 2 | 1 | 0 | 1 | −C(=O)−C$_6$H$_4$−OMe | 63~64 | 65 | C$_{15}$H$_{17}$NO$_3$ | 69.52 (69.48) | 6.72 (6.61) | 5.31 (5.40) |
| 3 | 1 | 0 | 2 | −C(=O)−C$_6$H$_4$−OMe | oil | 80 | C$_{16}$H$_{19}$NO$_3$ | 70.38 (70.31) | 7.03 (7.01) | 5.27 (5.12) |
| 3a | 1 | 0 | 2 | −C(=O)−C$_6$H$_4$−OMe | 93 | 15 | C$_{16}$H$_{19}$NO$_3$ | 70.21 (70.31) | 7.29 (7.01) | 5.05 (5.12) |
| 3b | 1 | 0 | 2 | −C(=O)−C$_6$H$_4$−OMe | 75 | 50 | C$_{16}$H$_{19}$NO$_3$ | 70.23 (70.31) | 7.00 (7.01) | 5.11 (5.12) |

TABLE 1-continued

| No. | l | m | n | R | m.p. (°C.) | yield (%) | formula | elementary analysis (%) C | H | N |
|---|---|---|---|---|---|---|---|---|---|---|
| 4 | 1 | 0 | 2 | −C(=O)−C₆H₄−Me (p) | 79~80 | 82 | $C_{16}H_{19}NO_2$ | 74.82 (74.68) | 7.70 (7.44) | 5.26 (5.44) |
| 5 | 1 | 0 | 2 | −C(=O)−C₆H₃(Cl)(Cl) | 82~83 | 90 | $C_{15}H_{15}NO_2Cl_2$ | 57.99 (57.71) | 4.98 (4.84) | 4.01 (4.49) |
| 6 | 1 | 0 | 2 | −C(=O)−C₆H₃(OMe)(OMe) | 78.5~79.5 | 81 | $C_{17}H_{21}NO_4$ | 67.46 (67.31) | 7.22 (6.98) | 4.33 (4.62) |
| 7 | 1 | 0 | 2 | −C(=O)−C₆H₄−CN | 148.5~149 | 83 | $C_{16}H_{16}N_2O_2$ | 71.71 (71.62) | 6.07 (6.01) | 10.39 (10.44) |
| 8 | 1 | 0 | 2 | −C(=O)−C₆H₄−NO₂ | 148~149 | 85 | $C_{15}H_{16}N_2O_4$ | 62.39 (62.49) | 5.70 (5.59) | 9.56 (9.72) |
| 9 | 1 | 0 | 2 | −C(=O)−C₆H₄−NH₂ | 132~134 | 65 | $C_{15}H_{18}N_2O_2 \cdot 1/7 H_2O$ | 7.23 (7.06) | 69.08 (69.06) | 10.77 (10.74) |
| 10 | 1 | 0 | 2 | −C(=O)−C₆H₄−Cl | 100~101 | 90 | $C_{15}H_{16}NO_2Cl$ | 64.82 (64.87) | 5.77 (5.81) | 5.19 (5.04) |
| 11 | 2 | 0 | 1 | −C(=O)−C₆H₄−OMe | oil | 79 | $C_{16}H_{19}NO_3$ | 68.98 (70.31) | 6.94 (7.01) | 5.00 (5.12) |
| 12 | 2 | 1 | 0 | −C(=O)−C₆H₄−OMe | 67~69 | 52 | $C_{16}H_{19}NO_3$ | 70.51 (70.31) | 7.07 (7.01) | 4.97 (5.12) |

TABLE 2

| Compound No. | ¹H-NMR (δ, ppm) (solvent: CDCl₃) |
|---|---|
| 3 | 1.27~2.70(11H, m), 3.83(3H, s), 4.30~4.62(1H, m), 6.78~7.69(4H, m) |
| 11 | 1.00~2.81(11H, m), 3.60~4.40(1H, m), 3.84(3H, s), 6.80~7.71(4H, m) |

TABLE 3

| | DOSE (mg/kg) | | | | |
|---|---|---|---|---|---|
| | 3 | 10 | 30 | 100 | 300 |
| Compound 3 | | 16 | 57 | 35 | 41 |
| Compound 12 | | 13 | 33 | 25 | 21 |
| Aniracetam | | 9 | 23 | 29 | 5 |

TEST EXAMPLE 2

Acute Toxicity Test

Mice (ddY, five-week-old males) were used in groups of 4 to 5 mice each. The test compound was dissolved or suspended in 0.5% solution of sodium carboxymethyl cellulose and administered orally. The mice were observed for 3 days to measure the number of deaths. Compound 3 was at least 2000 mg/kg in $LD_{50}$ and Compound 12 was at least 5000 mg/kg in $LD_{50}$. Industrial applicability The medicaments for treating senile dementia must have cerebral function improving activity to ameliorate memory and learning disturbances and activity to activate the metabolism of cerebral nerve cells or to protect these cells from injuries and attacks. It is further desired that the medicaments be diminished in side effects and of high safety since the patients are aged people. When fulfilling these requirements, the medicaments are useful for treating senile dementia.

Table 3 reveals that the present compound exhibit antiamnesia activity and further have two activites, i.e., activity to improve cerebral functions and activity to activate cerebral metabolism or protect anoxic brain damage.

To sum up, the present compounds have two pharmacological activities, i.e., cerebral function improving activity and cerebral metabolism activating or anoxic brain damage protecting activity, low toxicity and therefore usefulness and are effective for treating senile dementia.

We claim:

1. A bicyclolactam derivative represented by the formula

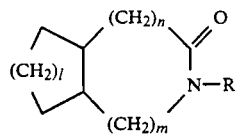

wherein R is benzoyl group which may be substituted with halogen atom, lower alkyl group, lower alkoxyl group, nitro group, cyano or amino group; l is 1; m is 0; and n is 1 or 2.

2. A bicyclolactam derivative as defined in claim 1 wherein R is benzoyl group which is substituted with lower alkoxyl group or amino group, l is 1, m is 0, and n is 2.

3. A bicyclolactam derivative as defined in claim 1 wherein R is benzoyl group which is substituted with lower alkoxyl group, l is 1, m is 0, and n is 2.

4. A cerebral function improving composition and a cerebral metabolism activating or anoxic brain damage protecting composition each comprising a pharmacologically acceptable carrier and an effective amount of the bicyclolactam derivative of claim 1.

5. A method of improving cerebral functions and activating cerebral metabolism or protecting anoxic brain damage characterized by administering to a patient an effective amount of the bicyclolactam derivative of claim 1.

* * * * *